United States Patent [19]
Blythe

[11] Patent Number: 6,080,118
[45] Date of Patent: Jun. 27, 2000

[54] VAGINAL PROBE AND METHOD OF USING SAME

[76] Inventor: Cleveland Blythe, 1106 Wilson Avenue, Toronto, Ontario, Canada, M3M 1G7

[21] Appl. No.: 09/257,201

[22] Filed: Feb. 25, 1999

[51] Int. Cl.[7] .................................................. A61B 5/103
[52] U.S. Cl. .......................................... 600/591; 600/549
[58] Field of Search ................................... 600/547, 549, 600/551, 552, 554, 555, 557, 570, 571, 587, 591, 593

[56] References Cited

U.S. PATENT DOCUMENTS

| | | | |
|---|---|---|---|
| 3,253,588 | 5/1966 | Vuilleumier | 600/547 |
| 5,061,272 | 10/1991 | Reese | 600/570 |
| 5,209,238 | 5/1993 | Sundhar . | |
| 5,499,631 | 3/1996 | Weiland . | |
| 5,820,263 | 11/1998 | Ciobanu | 600/549 |
| 5,916,173 | 6/1999 | Kirsner | 600/547 |

FOREIGN PATENT DOCUMENTS

| | | |
|---|---|---|
| 0386649 | 9/1990 | European Pat. Off. . |
| 0745853 | 12/1996 | European Pat. Off. . |
| 9423653 | 10/1994 | WIPO . |

OTHER PUBLICATIONS

Abtech Scientific, Inc. Internet Homepage www.abtechsci.com/abtechsci.html Dated Apr. 24, 1998 p. 1.
Abtech Scientific, Inc. Internet Homepage www.abtechsci.com/labproducts.html Dated Apr. 24, 1998 p. 1.
Abtech Scientific, Inc. Internet Homepage www.abtechsci.com/imes.html Dated Apr. 24, 1998 pp. 1 to 5.
Abtech Scientific, Inc. Internet Homepage www.abtechsci.com/epmes.html Dated Apr. 24, 1998 pp. 1 to 4.
Abtech Scientific, Inc. Internet Homepage www.abtechsci.com/babs.html Dated Apr. 24, 1998 pp. 1 to 5.
Abtech Scientific, Inc. Internet Homepage www.abtechsci.com/pmes.html Dated Apr. 24, 1988 pp. 1 to 4.

*Primary Examiner*—Max Hindenburg
*Attorney, Agent, or Firm*—Riches, McKenzie & Herbert

[57] ABSTRACT

A probe used to determine different possible body conditions of a human or animal subject includes an elongated insertable portion which is adapted for use orally, anally or vaginally, and along which are provided a number of biosensors and/or temperature sensors. The elongated portion is contoured so as to have a complementary shape to the physiology of the user's mouth, anus or vagina to ensure good contact between the probe sensors and the subject's body fluids or tissues. At least some of the sensors are positioned within a channel or trough which extends along the insertable portion of the probe and which is sized to collect body fluids from the subject therein. Preferably the channel is defined by a pair of spaced apart projecting ribs with fluid grooves formed in the elongated portion to assist in directing body fluids towards the channel and sensors. In use, once the probe is inserted, body fluids will tend to collect in the channel ensuring that the sensors therein are emersed in the fluid, eliminating air pockets and ensuring more accurate biosensor readings.

18 Claims, 3 Drawing Sheets

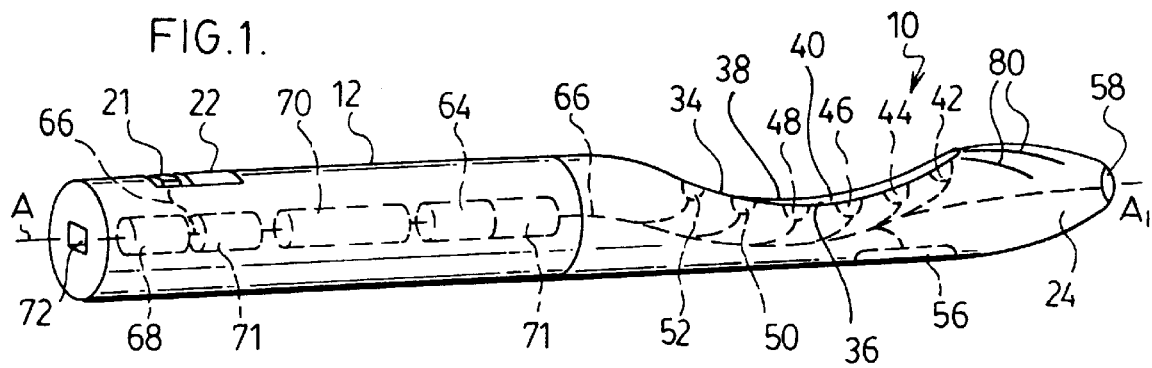
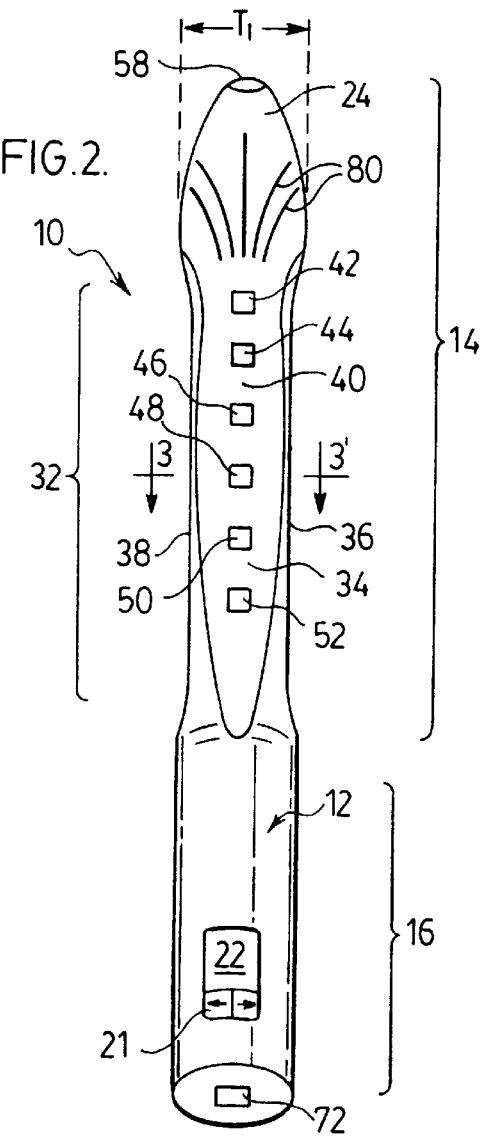
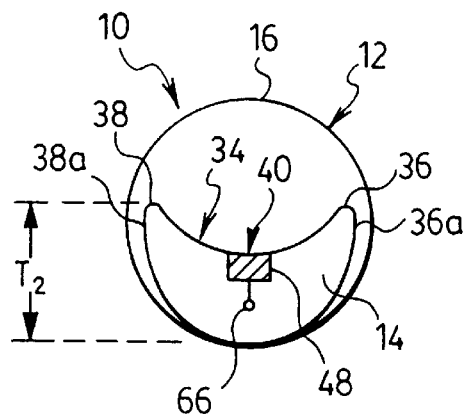

VAGINAL PROBE AND METHOD OF USING SAME

SCOPE OF THE INVENTION

The present invention relates to a probe used to determine the status of one or more body conditions of a human and/or animal subject, and more particularly a probe provided with a number of sensors which is adapted for insertion into the subject's mouth, vagina or anus to sense one or more body characteristics which are indicative of a given body condition, and a method of using such a probe.

BACKGROUND OF THE INVENTION

Vaginal or anal probes which are used to sense or measure a subject's body characteristics to provide an indication of a particular body condition are known. U.S. Pat. No. 5,209,238 to Sundhar, which issued May 11, 1993 discloses one prior art vaginal probe and is incorporated herein by reference. The probe of Sundhar consists of a cylindrically shaped housing which has positioned therealong a number of longitudinally spaced sensors. In its operation, the probe is used to determine whether or not a human female is ovulating by sensing the state of four body characteristics: basal body temperature; mucous density; pH level; and LH level. As a result of the sensed values, the user is provided with a visual output as to whether or not the received data is indicative of the presence of a viable egg.

The probe disclosed in U.S. Pat. No. 5,209,238 suffers certain disadvantages in that the cylindrical shape of the probe housing does not lend itself to the positioning of the sensors in close contact with the walls of the user's vagina. As a result, gaps may exist between the user's vaginal tissues and the sensors. This in turn may lead to false sensor readings indicating a user is not ovulating when she may be, or vice versa.

The difficulties associated with the Sundhar probe construction are further compounded if the user's vagina is dry. In such a case, air pockets may exist about the sensors, resulting in poor contact with the sensed vaginal fluids, increasing the likelihood of inaccuracies and misreadings.

SUMMARY OF THE INVENTION

The present invention seeks to overcome those disadvantages of prior art devices by providing a probe having at least one sensor for use in sensing a given body characteristic, and which is constructed so as to trap and/or collect the subject's body fluids about the probe sensors to ensure a high level of sensor/body fluid contact.

A further object is to provide a probe for sensing body characteristics of an animal or human subject and which is adapted for use either orally, vaginally and/or anally.

Another object of the invention is to provide a probe having one or more sensors for sensing a body characteristic which provides an indication of a user's existing body condition, and in which at least one of the sensors is positioned along a surface of the probe which substantially conforms to the physiology of the user's body at the point which the sensor is to be used.

Another object of the invention is to provide a probe having an end portion sized for insertion into a subject's vagina or anus, and which includes a number of sensors which may be operated either singularly or plurally, in various selected combinations, or simultaneously to sense various body characteristics of the subject which are indicative of different body conditions.

Another object of the invention to provide a vaginal probe used to sense a number of different and continuous possible body conditions in a human subject by the selective activation and deactivation of different sensors disposed thereon.

A further object of the invention is to provide a vaginal probe which may be used to sense body characteristics of an animal, and which includes a transponder signal receiver which permits the probe to be identified for use with an individual animal having a specific transponder signal transmitter.

In furtherance of at least some of the foregoing objects, the invention provides a probe having at least one, and preferably a number of sensors which are used to determine the status of one or more different and continuous body conditions of a human or animal subject. Possible body conditions to be determined by the probe include by way of non-limiting examples, the presence of the viable egg in a female subject, whether or not a female subject is ovulating, an indication of a probable pregnancy, and/or the presence of a possible disease or infection in the subject. In use of the probe, the sensors are operable to sense one or more of the subject's body characteristics which provide indications of the body condition to be determined. For example, the sensors may be used to sense body temperature, the pH level of sensed fluids, Luteinising hormone (LH) level of vaginal fluids, cervical mucous density, estrogen levels, progesterone levels, estradiol levels, vaginal cavity pressures, follicle stimulating hormone (fsh) levels, blood colouration, and/or human chorionic gonadotropohin (hCG) hormone levels. Data collected by the sensors is then processed and analyzed to determine the status of a particular body condition, and the calculated information respecting the status of the subject's body condition is output on a light emitting diode (LED), liquid crystal display (LCD) or by audio speaker provided as part of the probe, and/or presented on a computer screen which is linked to the probe.

The sensor or sensors are provided along a portion of the probe housing which is adapted for oral, anal or vaginal use. Most preferably, the probe has an elongated end portion which is sized to permit insertion into the subject's vagina. Suitable sensors may include temperature sensors as well as biosensors, electromagnetic radiation sensors, photovoltaic sensors, photoconductors and detectors, or thermal imaging arrays. Other types of sensors may also be used. The sensors are electronically coupled to integrated circuitry which is either housed within the probe housing itself, and/or an external computer by means of a connecting cable and interface port.

The insertable end portion of the probe is configured to ensure good contact between the probe sensors and the subject's body fluids and/or tissues. Preferably, at least some of the sensores are positioned within a channel or trough which extends along the insertable portion of the probe. As the probe is inserted into the subject's vagina, anus or mouth, any body fluids which are present will tend to collect in the channel ensuring that the sensors therein are emersed in the fluid. This advantageously eliminates air pockets, and false readings and ensures more accurate biosensor readings. In one preferred embodiment, the channel is defined by a pair of spaced apart projecting ribs which extend longitudinally in the direction of elongation of the insertable end portion of the probe, although other channel or rib configurations are also possible. The ribs permit the probe to be rotated about its longitudinal length following its insertion into the subject's vagina, anus or mouth to act as a scoop, and facilitate the collection of body fluids about the sensors within the channel. Optionally, one or more fluid flow grooves may also be formed across the insertable end portion of the probe, to assist in directing body fluids into the channel and towards the sensors therein.

More preferably, the insertable portion of the probe is contoured so as to have a complementary shape to fit the physiology of the subject's vagina, anus or mouth depending on where the sensor is to be placed. For example, where the sensor is to be used vaginally on a human subject, the probe may include a contoured portion which is characterized by a gently curving concave surface. The concave surface curves in a longitudinally extending arc and is configured for placement against the anterior wall of a woman's vagina, with at least one, and preferably the majority of the sensors and the channel positioned along the concave surface. In this manner, the insertable end portion of the probe follows the natural curvature of the anterior vaginal wall, ensuring close contact between probe sensors and the body tissues which make up the subject's vaginal walls.

Where the probe is to be used for veterinary applications, it is to be appreciated that the insertable end portion of the probe may be formed having a larger or smaller size, depending upon the animal with which the probe is intended to be used. In veterinary applications, the probe preferably also includes a transponder signal receiver adapted to receive a transponder signal from a transponder signal transmitter mounted on an animal collar or tag. In this manner, the probe may be electronically coded for use with a particular animal, so as to minimize the possibility of disease transmission to other animals.

Accordingly, in one aspect the present invention resides in a probe for determining a body condition of a human or animal subject comprising, a generally cylindrical housing, the housing being elongated along a longitudinal axis and having a first end portion sized for insertion into the subject's mouth, vagina or anus, and a second end portion, the first end portion including an end tip having a first minimum thickness, and a contoured portion spaced rearwardly from said end tip towards the second end portion, the contoured portion defined at least in part by a generally concave surface, said concave surface curving in a generally longitudinally extending arc with said contoured portion having a minimum thickness selected less than the first thickness, at least one sensor disposed along said concave surface for sensing a body characteristic of said subject which is indicative of said body condition and generating continuous data signals representative of said sensed body characteristic, The said sensors are linked to any integrated circuit for processing data signals, and an output electronically linked to said integrated circuit for outputting information representing the status of said body characteristic.

In another aspect, the present invention resides in a vaginal probe for determining a body condition of a human subject comprising, a housing elongated along a longitudinal axis and having a first end portion and a second end portion, the first end portion having an end tip and a contoured portion spaced rearwardly from said end tip towards the second end portion, the first end portion being sized to permit its insertion into the subject's vagina with said end tip locating adjacent to the subject's cervix, the contoured portion including a generally concave surface curving in a generally longitudinally extending arc, a plurality of axially spaced sensors disposed along said concave surface, at least one of said sensors for sensing a body characteristic which is indicative of said body condition and generating data signals representative of said sensed body characteristic, an integrated circuit electronically linked to said sensors for processing data signals received therefrom, and an output display electronically linked to said integrated circuit displaying information indicative of said body condition.

In a further aspect, the present invention resides in a vaginal probe for determining a body condition of a human or animal subject comprising, a housing having a first end portion elongated along a longitudinal axis and sized for insertion into the subject's vagina, and a second end portion, the first end portion including a channel sized to permit the collection of vaginal fluids therein, and at least one sensor located within said channel for sensing a body characteristic of said subject which is indicative of a body condition and generating data signals representative of said sensed body characteristic, an integrated circuit electronically linked to said at least one sensor for processing generated data signals, and an output linked to said integrated circuit for outputting information indicative of said body characteristic.

BRIEF DESCRIPTION OF THE DRAWINGS

Reference is now made to the following detailed description taken together with the accompanying drawings in which:

FIG. 1 is a schematic side view of a vaginal probe for use on a human subject in accordance with a preferred embodiment of the invention;

FIG. 2 is a perspective front view of the probe shown in FIG. 1;

FIG. 3 is a cross-sectional view of the probe shown in FIG. 2 taken along lines 3—3;

DETAILED DESCRIPTION OF THE INVENTION

Reference is first made to FIGS. 1 to 3 which show a vaginal probe 10 which is operable to determine the current status of a number of different body conditions of a human female patient, including whether or not the patient has conceived, the presence of possible diseases or infections, or whether or not the patient is currently ovulating or about to ovulate.

Figure 4:
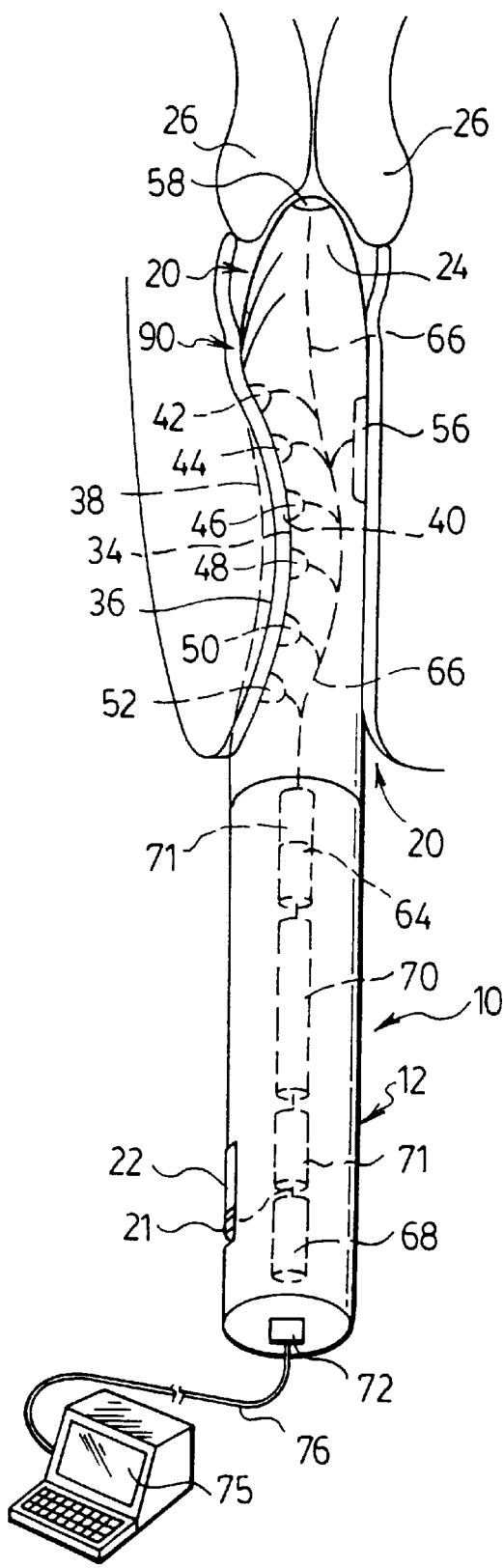
FIG. 4 illustrates schematically a side view showing the placement of the probe of FIG. 1 during sensor operation.

As seen best in FIGS. 1 and 2, the probe 10 comprises a molded plastic housing 12 which is formed having a generally cylindrical shape and which is elongated in a longitudinally direction along axis A–A$_1$ (FIG. 1). As shown in FIG. 2, the housing consists of an insertable end portion 14 which is sized for insertion into a woman's vagina 20 (FIG. 4) and an external end portion 16 along the exterior of which are provided controls 21 used to operate the probe 10 and a liquid crystal display (LCD) 22. The controls 21 include switches used to turn the probe 10 off or on, as well as switches used to select a specific body condition to be sensed. The insertable end portion 14 has a maximum lateral thickness $T_1$ (FIG. 2) selected at between about 0.5 and 2 cm, and preferably about 1 cm. The insertable end portion 14 extends from an endmost tip 24 rearwardly to merge into the exterior end portion 16, and has an overall axial length of between about 5 and 15 cm. As will be described hereafter with reference to FIG. 4, the length of the insertable portion 14 is selected so that when the end portion 14 is fully inserted into the patient's vagina 20, the tip 24 locates immediately adjacent and most preferably in contact with the patient's cervix 26 (FIG. 4).

Rearwardly from the tip 24, the insertable end portion 14 is provided with a contoured portion 32 (FIG. 2) which is configured to provide a complementary shape and size to the physiology of the patient's vagina 20. The contoured portion 32 includes a concave surface 34. The concave surface 34 curves gently as a longitudinally extending arc a distance of approximately 5 to 8 cm. The curvature of the concave surface 34 is generally complementary to the curvature of part of the patient's vagina 20 (FIG. 4). As shown best in FIG. 3, the minimum thickness $T_2$ of the contoured portion 32 taken through its middle is less than the maximum lateral thickness $T_1$, of the end portion 14 taken through the end tip 24, and most preferably has a dimension of between about 0.25 and 1 cm.

A pair of spaced apart ribs 36,38 extend longitudinally along each side of the concave surface 34. FIG. 3 shows best the ribs 36,38 projecting from each edge of the concave surface 34 approximately 1 to 2 mm to define a longitudinally extending trough or channel 40 therebetween. The channel 40 is sized to permit the collection of the patient's vaginal fluids therein, and most preferably has a width selected at approximately 1 cm and a length which extends ¾ the length of end portion 14. The outer side surface 36a,36b of each rib 36,38 is rounded, so as to permit substantially unrestricted movement of the patient's vaginal fluids past the surfaces 36a,36b on rotation of the probe 10 about the longitudinal axis A–$A_1$.

Six longitudinally spaced apart sensors 42,44,46,48,50,52 are positioned axially aligned with each other along the center of the channel 40. By way of non-limiting examples, suitable sensors for use with the probe 10 would include photovolatic sensors such as those manufactured by Sensors Unlimited, Inc., electro-optic detectors including photoconductors, photodiodes, thermophile and pyroelectric sensors such as those sold under the name EPNE™ by Abtech Laboratories Products, as well as chemoresistance sensors and bio-analytical biotransducers. It is to be appreciated that the curvature of the concave surface 34, and extent the ribs 36,38 project therefrom are most preferably selected to conform to the curvature of part of the patient's anterior vaginal wall 90 (FIG. 4) to ensure that, when inserted, the sensors 42,44,46,48,50,52 are maintained in close contact therewith. This advantageously and substantially eliminates any air pockets between the sensors 42,44,46,48,50,52 and the patient's vaginal tissues which may give rise to false sensor readings.

Sensor 42 is a biosensor used to sense human chorionic gonadotrophin (hCG) levels in the patient's vaginal fluids. hCG hormones produced during pregnancy are detectable in the blood or urine 1 to 2 days after implantation (10 days after ovulation). This hormone increases rapidly in the first trimester, reaching a peak 60 to 80 days after fertilization; then drops off quickly to 10 to 30% of the peak value for the rest of the pregnancy. It serves to maintain progesterone production by the corpus luteum in the early part of pregnancy. By the time hCG drops at the beginning of the second trimester, the placenta can make sufficient progesterone to maintain the endometrium. In general, a sensed hCG level of less than 5 mIU/ml would be generally indicative that the patient was not pregnant.

Sensor 44 comprises an ultrasound sensor used to sense Luteinising hormone (LH) levels. As disclosed in U.S. Pat. No. 5,209,238 to Sundhar, by ascertaining the amplitude of reflected ultrasonic energy from vaginal tissues, it is possible to ascertain the presence of LH levels in the patient. These levels in turn may be used to correlate whether or not the patient may be currently ovulating.

Sensor 46 is an estrogen biosensor which is used to ascertain the levels of one or more of estradiol, estrone, and estriol in the patient's vaginal fluids. Sensor 48 also consists of a biosensor used to sense progesterone levels in the patient's vaginal fluids, and may be used in conjunction with sensor 46 to evaluate whether or not the patient has conceived or about to start ovulation. Like estrogen, progesterone is made in the ovaries. Progesterone production begins rising at ovulation and increases rapidly until it reaches an average production of about 22 milligrams per day. If an egg is not fertilized, progesterone production (as well as that of estrogen) falls quickly. This initiates the menstrual flow. Progesterone is necessary for the survival of a fertilized egg, the resulting embryo, and the fetus throughout gestation. It is also the precursor of other steroid hormones including cortisol, aldosterone, estrogen, and testosterone. Progesterone has many other functions, among them protecting against breast fibrocysts, helping the body use fat for energy, and helping to normalize blot clotting and blood sugar levels.

Sensor 50 operates as either a UTI sensor or pH sensor to measure acidity or alkalinity via the electrical potential of the vaginal fluids.

Sensor 52 consists of biosensor used to sense the presence of a possible disease in the patient.

In addition, FIG. 1 shows best the probe 10 as also including a basal body temperature (BBT) sensor 56. The BBT sensor 56 is located immediately rearward of the end tip 24 along part of the contoured portion 32, and preferably, the basal body temperature sensor 56 is disposed on a side of the insertable portion 14 which is radially opposite from the concave surface 34.

An ultrasonic sensor 58 is also provided at the forwardmost end of the tip 24. The sensor 58 operates as a cervical mouth opening sensor which senses the presence of thicker mucous which is typically present when the cervix 26 (FIG. 4) is open. In this manner, the energy level of ultrasound energy reflected from the cervix 26 may be used to determine whether or not the cervix 26 is in an open or closed state. If the cervix 26 is closed and mucous is thicker, the reflected signal to the sensor 58 would typically be stronger than that compared when the cervix 26 is open.

The sensors 42,44,46,48,50,56,58 are each electronically coupled to an integrated circuit 64 (FIG. 1) contained within the housing 12 by lead wires 66. Power to the probe 10 and sensors 42,44,46,48,50,52,56,58 is supplied by an internal battery 68. An internal memory chip 70 is also contained within the housing 12. The memory chip 70 is used to store previous data from the patient by date, time and type of data, and permit a comparison of stored data from currently sensed data. Optionally, one or more amplifiers 71 may also be housed within the external end portion 16 of the probe 10 for use in amplifying the sensor signals. The wires 66 also electronically link the controls 21 and LCD 22 to the integrated circuit 64, battery 68 and memory chip 70. In this manner the controls 21 are used to selectively actuate and/or receive data from one or a combination of sensors 42,44, 46,48,50,52,56,58, depending upon the patient's body condition to be determined. The controls 21 are also configured to automatically turn the probe 10 to a "power off" state after a predetermined period of over-use, to preserve battery 68 life.

In a preferred embodiment, the probe 10 is designed for both portable as well as in clinic use by both professional staff as well as by the patent directly. In addition to the internal battery 68, the integrated circuit 64 is also connected to a computer interface port 72 located on the external end portion 16 of the probe 10. The interface port 72 permits the probe 10 to be linked to a personal computer 75 via control cable 76 in the manner shown in FIG. 4. The computer 75 may be used in the control of and/or to receive output from the probe 10 to visually indicate the status of the patient's body condition which is sensed. Patient data and medical history 8 is preferably also stored in the computer 75, including for example, information as to the patient's name, social security data, age, known allergies. Optimally, the personal computer 75 may also be used to store data from previous diagnostic tests to permit a user to chart changes in the sensed body characteristics and, for example, provide an indication of a likely pregnancy or the like.

FIGS. 1 and 2 show best the insertable portion 14 of the probe 10 as also including a number of fluid flow grooves 80. The fluid flow grooves 80 are formed in the housing 12 in a generally longitudinal orientation across the end tip 24, and extend substantially towards the channel 40. The grooves 80 preferably have approximate dimensions of 0.5 to 1 mm in both lateral width and depth and permit the substantially unrestricted movement of vaginal fluid therealong.

The operation of the probe 10 is shown with reference to FIG. 4. In use, the insertable end portion 14 of the probe 10 is inserted into the subject's vagina 20 so that the endmost tip 24 makes contact with the outer end of the patient's cervix 26, and with the external end portion 16 maintained external to the patient. The positioning of the basal body temperature sensor 56 on the probe 10 at a position radially spaced from the concave surface 34 advantageously keeps the sensor 56 in constant contact with the vaginal tissues as the insertable end portion 14 is inserted into the patient's vagina 20. When the probe 10 is inserted into a subject's vagina 20, if the cervix 26 is closed the end tip 24 may be used to apply pressure against the closed cervix 26 to facilitate the escape of fluids therefrom. Any fluids escaping from the cervix 26 flow directly along the fluid grooves 80 and into the channel 40, to ensure complete emersion of sensors 42,44,46,48,50,52 located therein.

If on initial placement of the end portion 14 the subject's vagina 20 is dry, the probe 10 is rotated about its longitudinal axis A–A$_1$. As the probe 10 is rotated, the ribs 36,38 further act to collect any vaginal fluids which are present about the probe 10 within the channel 40. The rotation of the probe 10 may also achieve the added benefit of stimulating the secretion of vaginal fluids. Where the probe 10 is used vaginally on a human female, following its rotation, the probe 10 is positioned so that the concave surface 34 and sensors 42,44,46,48,50,52 are moved into juxtaposition with the anterior vaginal wall 90 of the patient's vagina 20. In this position, the basal body temperature sensor 56 locates in contact with the posterior vaginal wall 92.

The desired sensors 42,44,46,48,50,52,56,58 are then actuated by means of either the controls 21 on the exterior portion 16 of the probe 10, or via the computer 75 if the interface port 72 is used to sense the desired body characteristic. It is to be appreciated that the sensors 42,44,46,48, 50,52,56,58 may be operated independently depending upon which body condition is to be analyzed, or simultaneously for an overall diagnostic analysis. Alternately, all of the sensors 42,44,46,50,52,56,58 may be continuously operated and the integrated circuit 64 used to selectively screen and analyze data signals therefrom, depending on the body condition to be sensed. Following their activation, data received from the sensors 42,44,46,48,50,52,56,58 is processed by the integrated circuit 64 (or by the computer 75) to determine the status of the particular body condition, and the status of the body condition in their output to the user via the LCD 22. Data output from each sensor 42, 44, 46, 50, 52, 56, 58 is compared and validated against each other to ensure an accurate and true reading by the probe 10.

For example, the sensors may be used to sense human chorionic gonadotrophin (hCG) hormone to determine whether or not the patient is pregnant. It is generally believed if pregnant, hCG numbers will tend to increase following pregnancy. The probe 10 and either the integrated circuit 64 or computer 75 may thereby be used to analyze two consecutive hCG tests immediately following ovulation as an indicator of unlikely pregnancy.

Figure 5:
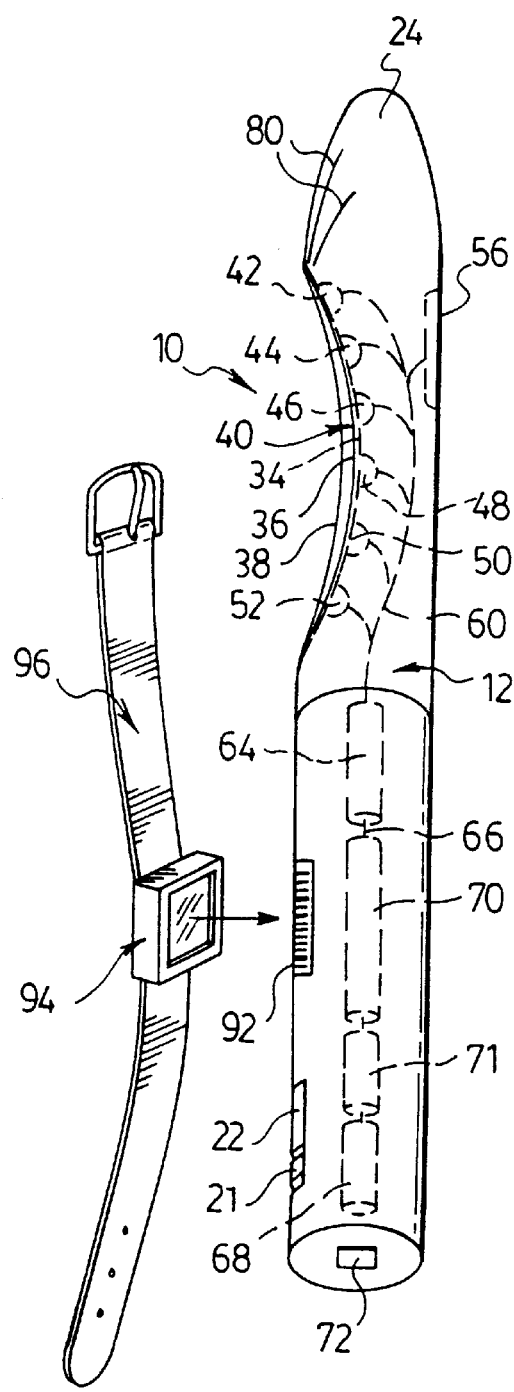
FIG. 5 is a schematic view of a probe for use on an animal subject in accordance with a second aspect of the invention.

FIG. 5 illustrates a modified probe for use in veterinary applications, and wherein like reference numerals are used to identify like components. Like the apparatus shown in FIG. 1, the apparatus of FIG. 5 is adapted to be used as either a stand alone unit, or in a clinical environment if connected to a computer in the manner shown in FIG. 4. In a more economical model, however, the probe 10 could be provided without the computer interface port 72 restricting the probe 10 to portable in field use.

The probe 10 of FIG. 5 is typically larger in size than the probe 10 of FIG. 1 described for human use. The probe 10 of FIG. 5 is shown without an ultrasound sensor 58, and could optionally include fewer or more sensors 42,44,46, 48,50,52,56 depending upon the characteristics to be sensed. The probe 10 is additionally provided with an internal transponder signal receiver 92 which is electronically linked to the LCD display 22 via the memory chip 70 and lead wires 66. The transponder signal receiver 92 is adapted to receive a signal from a transponder signal transmitter 94 which is mounted on a collar 96 to be secured to a subject animal. The transponder signal receiver 92 advantageously permits the user to identify precisely which animal out of a herd is to be diagnosed with the probe 10. Where highly contagious diseases may be present in a herd, the transponder signal receiver 92 is used to isolate the probe 10 for use with the infected animal, minimizing the likelihood of cross-infection between the herd animals. In addition, the probe 10 memory chip 70 is selectively operable for each coded transponder signal to provide a stored data base of diagnostics for a number of different herd animals.

Although the preferred embodiment of the invention illustrates the probe as having six or eight sensors 42,44, 46,48,50,52 disposed within the channel 40, a basal body temperature sensor 56 and ultrasonic sensor 58, the invention is not so limited. If desired, the probe 10 could equally include fewer or more sensors without departing from the spirit and scope of the present invention. Similarly, while the preferred embodiment discloses the probe 10 as sensing specific body characteristics of a subject, it is to be appreciated that different types of sensors may be used to sense other body characteristics depending on the body condition which is to be analyzed.

Figure 6:
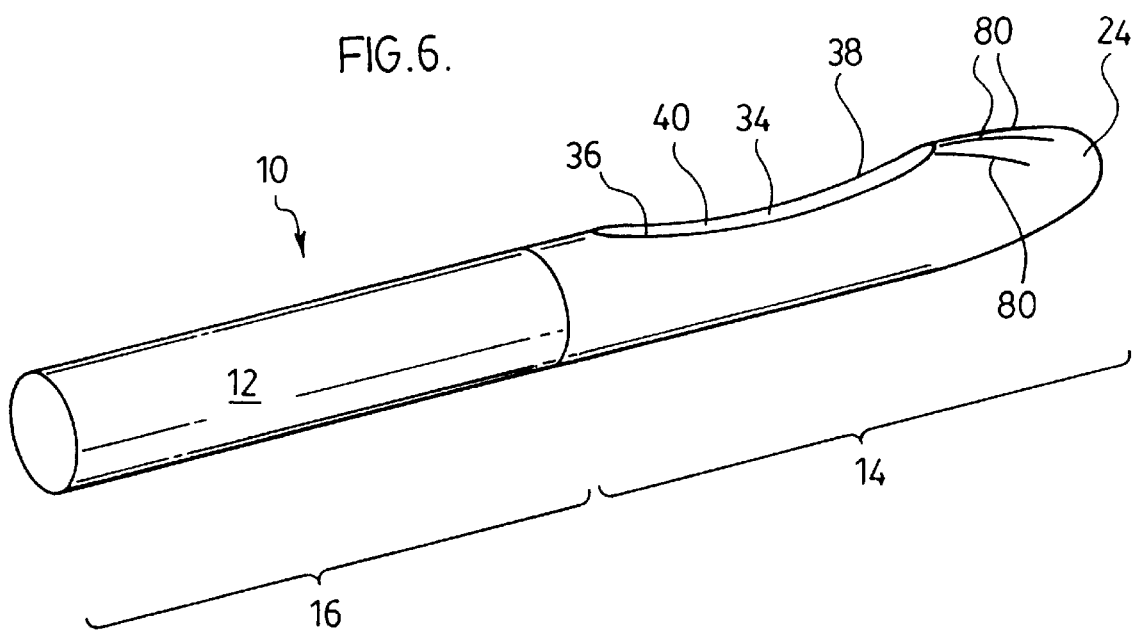
FIG. 6 is a schematic view of a probe for use on a human or animal in accordance with a third aspect of the invention.

FIG. 6 shows another modified probe 10 used to facilitate artificial insemination of a human or animal subject, and where in like reference numerals and used identify like opponents. FIG. 6 illustrates the probe 10 as having the same general overall configuration as the probe shown in FIG. 1, albeit without sensors, controls or a LCD display.

In use of the probe 10 of FIG. 6, semen is positioned in the fluid flow grooves 80 and/or the channel 40. Thereafter, the probe 10 is inserted in the subject's vagina to deliver the semen towards the subject's cervix. Alternately, an axially elongated probe 10 could be used to deliver a fertilized egg into the subject's vagina for implantation in the patient's uterus.

While the preferred embodiment of the invention illustrates the sensors 42,44,46,48,50,52 as being positioned within a generally longitudinally extending channel 40, the invention is not so limited. If desired the channel 40 could equally be provided in a generally laterally extending orientation, or as having an irregular or sinuously extending shape, without departing from the spirit and scope of the present invention.

Similarly, while the preferred embodiment of FIG. 2 illustrates the contoured portion 32 as including a concave surface 34 as a preferred construction for use with a human subject, other contour configurations are also possible depending upon the intended animal subject with which the probe 10 is to be used.

Although the detailed description describes and illustrates various preferred embodiments, the invention is not so limited. Many modifications and variations will now occur to persons skilled in the art. For a more precise definition of the invention, reference may be had to the appended claims.

We claim:

1. A probe for determining a body condition of a human or animal subject comprising, a generally cylindrical housing, the housing being elongated along a longitudinal axis and having a first end portion sized for insertion into the subject's mouth, vagina or anus, and a second end portion, the first end portion including an end tip having a first thickness, and a contoured portion spaced rearwardly from said end tip towards the second end portion, the contoured portion defined at least in part by a generally concave surface, said concave surface curving in a generally longitudinally extending arc with said contoured portion having a minimum thickness selected less than the first thickness, at least one sensor disposed along said concave surface for sensing a body characteristic of said subject which is indicative of said body condition and generating data signals representative of said sensed body characteristic, said contoured portion further including a pair of spaced apart ribs extending longitudinally along at least part of said concave surface to define a channel therebetween, said at least one sensor being disposed within said channel, an integrated circuit for receiving said data signals from each of said sensors and for processing said data signals, and an output electronically linked to said integrated circuit for outputting information representing the status of said body characteristic.

2. A probe as claimed in claim 1 wherein a plurality of sensors are axially spaced from each other along said concave surface, and said probe further comprising an ultrasonic sensor located at a forwardmost end of said end tip, said ultrasonic sensor being electronically linked to said integrated circuit.

3. A probe as claimed in claim 1 wherein a plurality of sensors are axially aligned with each other along said concave surface.

4. A probe as claimed in claim 1 further including a basal body temperature sensor, said basal body temperature sensor disposed along a portion of said first end portion radially spaced from said concave surface.

5. A probe as claimed in claim 3 wherein said body characteristic is selected from the group consisting of body temperature, pH level, Luteinising hormone level, mucous density, vaginal cavity pressure, estrogen level, progesterone level, and human chorionic gonadotrophin hormone level.

6. A probe as claimed in claim 5 wherein said output comprises a LCD display located in the second end portion of said housing for visually outputting said information.

7. A probe as claimed in claim 2 wherein, said sensors are disposed at axially spaced locations along said channel.

8. A probe as claimed in claim 7, wherein said first end portion further includes at least one groove extending in a genarally axial direction across said end tip substantially to said channel.

9. A probe as claimed in claim 1 wherein said subject is an animal, and said probe further includes a transponder signal receiver for receiving and identifying a signal from an animal transponder signal transmitter.

10. A vaginal probe for determining a body condition of a human subject comprising, a housing elongated along a longitudinal axis and having a first end portion and a second end portion, the first end portion having an end tip and a contoured portion spaced rearwardly from said end tip towards the second end portion, the first end portion being sized to permit its insertion into the subject's vagina with said end tip locating adjacent to the subject's cervix, the contoured portion including a generally concave surface curving in a generally longitudinally extending arc, a plurality of axially spaced sensors disposed along said concave surface, at least one of said sensors for sensing a body characteristic which is indicative of said body condition and generating data signals representative of said sensed body characteristic, said contoured portion further including a pair of ribs, said ribs being spaced from each other and extending longitudinally along at least part of said concave surface to define a channel therebetween, said sensors being disposed at axially spaced locations along said channel, an integrated circuit for receiving data signals from said sensors and for processing said data signals received therefrom, and an output display electronically linked to said integrated circuit displaying information indicative of said body condition.

11. A probe as claimed in claim 10, wherein said first end portion fuher includes at least one groove extending in a generally axial direction across said end tip substantially to said channel.

12. A probe as claimed in claim 11, wherein said sensors are selectively operable independently from each other depending on the body characteristic to be sensed.

13. A probe as claimed in claim 12, wherein said body characteristic is selected from the group consisting of body temperature, pH level, Luteinising hormone level, mucous density, estrogen level, progesterone level, and human chorionic gonadotrophin hormone level.

14. A probe as claimed in claim 10, further including a basal body temperature sensor, said basal body temperature sensor disposed along a portion of said first end portion radially spaced from said concave surface.

15. A probe as claimed in claim 14, wherein said sensors comprise at least one biosensor for sensing covalent immubilization of haptens, polypeptides, enzymes, antibodies and DNA fragments, and said probe further includes an ultrasonic sensor disposed towards a forwardmost end of said end tip, said ultrasonic sensor electronically linked to said integrated circuit.

16. A vaginal probe for determining a body condition of a human or animal subject comprising, a housing having a first end portion elongated along a longitudinal axis and sized for insertion into the subject's vagina, and a second end portion, the first end portion including a channel sized to permit the collection of vaginal fluids therein, and at least one sensor located within said channel for sensing a body characteristic of said subject which is indicative of a body condition and generating data signals representative of said sensed body characteristic, an integrated circuit electronically linked to said at least one sensor for processing generated data signals, and an output linked to said integrated circuit for outputting information indicative of said body characteristic.

17. A vaginal probe as claimed in claim 16, wherein said channel is defined in part by a pair of spaced apart longitudinally extending ribs, each of said ribs projecting radially outwardly from an immediately adjacent portion of said housing.

18. A vaginal probe as claimed in claim 16, wherein said first end portion further includes at least one fluid flow groove extending in a generally axial direction to assist in the flow of said vaginal fluids into said channel.

* * * * *